(12) United States Patent
Bridges et al.

(10) Patent No.: US 6,344,455 B1
(45) Date of Patent: Feb. 5, 2002

(54) N-[4-(3-CHLORO-4-FLUORO-PHENYLAMINO)-7-(3-MORPHOLIN-4-YL-PROPOXY)-QUINAZOLIN-6-YL]-ACRYLAMIDE, AND IRREVERSIBLE INHIBITOR OF TYROSINE KINASES

(75) Inventors: Alexander James Bridges, Saline; Denise Driscoll, Ann Arbor; Wayne Daniel Klohs, Ypsilanti, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/831,991
(22) PCT Filed: Sep. 23, 1999
(86) PCT No.: PCT/US99/22116
§ 371 Date: May 16, 2001
§ 102(e) Date: May 16, 2001
(87) PCT Pub. No.: WO00/31048
PCT Pub. Date: Jun. 2, 2000

Related U.S. Application Data
(60) Provisional application No. 60/109,065, filed on Nov. 19, 1998.

(51) Int. Cl.$^7$ ............ A61K 31/5377; A61P 35/00
(52) U.S. Cl. ............................... 514/234.5; 544/119
(58) Field of Search ................. 544/119; 514/234.5

(56) References Cited

FOREIGN PATENT DOCUMENTS

WO    WO 97 38983    * 10/1997

* cited by examiner

*Primary Examiner*—Robert W. Ramsuer
(74) *Attorney, Agent, or Firm*—Rosanne Goodman

(57) ABSTRACT

This invention relates to the compound N-[4-(3-chloro4-fluoro-phenylamino)-7-(3-morpholin-4-yl-propoxy)-quinazolin-6-yl]-acrylamide that is an irreversible inhibitor of tyrosine kinases. This invention also relates to a method of treating cancer, atherosclerosis, restenosis, endometriosis, and psoriasis using the compound N-[4-(3-chloro4-fluoro-phenylamino)-7-(3-morpholin4-yl-propoxy)-quinazolin-6-yl]-acrylamide, and to a pharmaceutical composition that comprises the compound N-[4-(3-chloro4-fluoro-phenylamino)-7-(3-morpholin-4-yl-propoxy)-quinazolin-6-yl]-acrylamide.

15 Claims, No Drawings

N-[4-(3-CHLORO-4-FLUORO-PHENYLAMINO)-7-(3-MORPHOLIN-4-YL-PROPOXY)-QUINAZOLIN-6-YL]-ACRYLAMIDE, AND IRREVERSIBLE INHIBITOR OF TYROSINE KINASES

This application is a 371 of PCT/US 99/22116 filed Sep. 23, 1999, which claims the benefit of Ser. No. 60/109,065 filed Nov. 19, 1998.

FIELD OF THE INVENTION

This invention relates to the compound N-[4-(3-chloro-4-fluoro-phenylamino)-7-(3-morpholin-4-yl-propoxy)-quinazolin-6-yl]-acrylamide that is an irreversible inhibitor of tyrosine kinases. This invention also relates to a method of treating cancer, atherosclerosis, restenosis, endometriosis, and psoriasis using the compound N-[4-(3-chloro-4-fluoro-phenylamino)-7-(3-morpholin-4-yl-propoxy)-quinazolin-6-ylj-acrylamide, and to a pharmaceutical composition that comprises the compound N-[4-(3-chloro-4-fluoro-phenylamino)-7-(3-morpholin-4-yl-propoxy)-quinazolin-6-yl]-acrylamide.

BACKGROUND OF THE INVENTION

Cancer has been viewed as a disease of the intracellular signaling system, or signal transduction mechanism. Cells receive instructions from many extracellular sources, instructing them to either proliferate or not to proliferate. The purpose of the signal transduction system is to receive these and other signals at the cell surface, get them into the cell, and then pass the signals on to the nucleus, the cytoskeleton, and transport and protein synthesis machinery.

The most common cause of cancer is a series of defects, either in these proteins, when they are mutated, or in the regulation of the quantity of the protein in the cell such that it is over or under produced. Most often, there are key lesions in the cell which lead to a constitutive state whereby the cell nucleus receives a signal to proliferate, when this signal is not actually present. This can occur through a variety of mechanisms. Sometimes the cell may start to produce an authentic growth factor for its own receptors when it should not, the so-called autocrine loop mechanism. Mutations to the cell surface receptors, which usually signal into the cell by means of tyrosine kinases, can lead to activation of the kinase in the absence of ligand, and passing of a signal which is not really there. Alternatively, many surface kinases can be overexpressed on the cell surface leading to an inappropriately strong response to a weak signal. There are many levels inside the cell at which mutation or overexpression can lead to the same spurious signal arising in the cell, and there are many other kinds of signaling defects involved in cancer. This invention touches upon cancers which are driven by the three mechanisms just described, and which involve cell surface receptors of the epidermal growth factor receptor tyrosine kinase family (EGFR). This family consists of the EGF receptor (also known as erbB1), the erbB2 receptor, and its constitutively active oncoprotein mutant Neu, the erbB3 receptor and the erbB4 receptor. Additionally, other biological processes driven through members of the EGF family of receptors can also be treated by compounds of the invention described below.

The EGFR has as its two most important ligands Epidermal Growth Factor (EGF) and Transforming Growth Factor alpha (TGFalpha). The receptors appear to have only minor functions in adult humans, but are apparently implicated in the disease process of a large portion of all cancers, especially colon and breast cancer. The closely related erbB2 (HER2), erbB3 (HER3), and erbB4 (HER4) receptors have a family of Heregulins as their major ligands, and receptor overexpression and mutation have been unequivocally demonstrated as the major risk factor in poor prognosis breast cancer. Additionally, it has been demonstrated that all four of the members of this family of receptors can form heterodimeric signaling complexes with other members of the family, and that this can lead to synergistic transforming capacity if more than one member of the family is overexpressed in a malignancy. Overexpression of more than one family member has been shown to be relatively common in human malignancies.

In addition to cancer, restenosis is also a disease in which undesired cellular proliferation occurs. Restenosis involves the proliferation of vascular smooth muscle cells. Restenosis is a major clinical problem associated with coronary angioplasty and other medical procedures. Restenosis generally occurs within about 0 to 6 months in about 30% to 50% of patients who undergo balloon angioplasty to clear clogged coronary arteries in an effort to treat heart disease due to occluded arteries. The resulting restenosis causes substantial patient morbidity and health care expense.

The process of restenosis is initiated by injury of the blood vessel, including arteries and veins, with the subsequent release of thrombogenic, vasoactive, and mitogenic factors. Endothelial and deep vessel injury leads to platelet aggregation, thrombus formation, inflammation, and activation of macrophages and smooth muscle cells. These events induce the production of and release of growth factors and cytokines, which in turn may promote their own synthesis and release from target cells. Thus, a self-perpetuating process involving growth factors such as EGF, platelet derived growth factor (PDGF) or fibroblast growth factor (FGFs) is initiated. Thus, it would be useful to have irreversible inhibitors of signal transduction pathways, particularly of tyrosine kinases like EGF, PDGF, FGF, or src tyrosine kinases.

The proliferative skin disease psoriasis has no good cure at present. It is often treated by anticancer agents such as methotrexate, which have very serious side effects, and which are not very effective at the toxicity limited doses which have to be used. It is believed that TGF alpha is the major growth factor overproduced in psoriasis, since 50% of transgenic mice which over express TGF alpha develop psoriasis. This suggests that a good inhibitor of EGFR signalling could be used as antipsoriatic agent, preferably, but not necessarily, by topical dosing.

It is especially advantageous to have irreversible tyrosine kinase inhibitors when compared to reversible inhibitors, because irreversible inhibitors can be used in prolonged suppression of the tyrosine kinase, limited only by the normal rate of receptor resynthesis, also called turnover.

Information on the role of src tyrosine kinases in biological processes relating to cancer and restenosis can be found in the following documents, which are all hereby incorporated by reference.

Benjamin C. W. and Jones D. A, Platelet-Derived Growth Factor Stimulates Growth Factor Receptor Binding Protein-2 Association With Src In Vascular Smooth Muscle Cells, *JBC*, 1994;269:30911–30916.

Kovalenko M., et al., Selective Platelet-Derived Growth Factor Receptor Kinase Blockers Reverse Cis-transformation, *Cancer Res*, 1994;54:6106–6114.

Schwartz R.S., et al., The Restenosis Paradigm Revisted: An Alternative Proposal for Cellular Mechanisms, *J Am Coll Cardiol*, 1992;20:1284–1293.

Libby P., et al., Cascade Model for Restenosis—A Special Case of Atherosclerosis Progression, *Circulation*, 1992;86:47–52.

Additional information on the role of EGF tyrosine kinases in biological processes relating to cancer and restenosis can be found in the following document which is hereby incorporated by reference.

Jonathan Blay and Morley D. Hollenberg, Heterologous Regulation Of EGF Receptor Function In Cultured Aortic Smooth Muscle Cells, *Eur J Pharmacol, Mol Pharmacol Sect*, 1989; 172(1): 1–7.

Information that shows that antibodies to EGF or EGFR show in vivo antitumor activity can be found in the following documents which are hereby incorporated by reference.

Modjtahedi H., Eccles S., Box G., Styles J., Dean C, Immunotherapy Of Human Tumour Xenografts Overexpressing The EGF Receptor With Rat Antibodies That Block Growth Factor-Receptor Interaction, *Br J Cancer*, 1993;67:254–261.

Kurachi H., Morishige K. I., Arnemiya K., Adachi H., Hirota K., Miyake A., Tanizawa O, Importance Of Transforming Growth Factor Alpha/Epidermal Growth Factor Receptor Autocrine Growth Mechanism In An Ovarian Cancer Cell Line In Vivo, *Cancer Res*, 1991;51:5956–5959.

Masui H., Moroyama T., Mendelsohn J, Mechanism Of Antitumor Activity In Mice For Anti-Epidermal Growth Factor Receptor Monoclonal Antibodies With Different Isotypes, *Cancer Res*, 1986;46:5592–5598.

Rodeck U., Herlyn M., Herlyn D., Molthoff C., Atkinson B., Varello M., Steplewski Z., Koprowski H., Tumor Growth Modulation By A Monoclonal Antibody To The Epidermal Growth Factor Receptor: Immunologically Mediated And Effector Cell-Independent Effects, *Cancer Res*, 1987;47:3692–3696.

Guan E., Zhou T., Wang J., Huang P., Tang W., Zhao M., Chen Y., Sun Y, Growth Inhibition Of Human Nasopharyngeal Carcinoma In Athymic Mice By Anti-Epidermal Growth Factor Receptor Monoclonal Antibodies, *Internat J Cell Clon*, 1989;7:242–256.

Masui H., Kawamoto T., Sato J.D., Wolf B., Sato G., Mendelsohn J, Growth Inhibition Of Human Tumor Cells In Athymic Mice By Anti-Epidermal Growth Factor Receptor Monoclonal Antibodies, *Cancer Res*, 1984;44:1002–1007.

In addition, the following documents show the antitumor activity of protein tyrosine kinase inhibitors. The documents are hereby incorporated by reference.

Buchdunger E., Trinks U., Mett H., Regenass U., Muller M., Meyer T., McGlynn E., Pinna L. A., Traxler P., Lydon N.B. 4,5-Dianilinophthalimide: A Protein Tyrosine Kinase Inhibitor With Selectivity For The Epidermal Growth Factor Receptor Signal Transduction Pathway And Potent In Vivo Antitumor Activity, *Proc Natl Acad Sci USA*, 1994;91:2334–2338.

Buchdunger E., Mett H., Trinks U., Regenass U., Muller M., Meyer T., Beilstein P., Wirz B., Schneider P., Traxler P., Lydon N. 4,5-Bis(4-Fluoroanilino)Phthalimide: A Selective Inhibitor Of The Epidermal Growth Factor Receptor Signal Transduction Pathway With Potent In Vivo Mdd Antitumor Activity, *Clinical Cancer Research*, 1995;1:813–821.

Compounds that are reversible inhibitors of tyrosine kinases have been described in U.S. Pat. Nos. 5,457,105, 5,475,001, and 5,409,930 and in PCT publication Numbers WO 9519774 and WO 9519970. The presently disclosed compound, which is structurally different from the tyrosine kinase inhibitors described in the above-identified documents, is an irreversible inhibitor of tyrosine kinases.

PCT Application Number PCT/US97/05778 (Publication Number WO 97/38983), which is hereby incorporated by reference, discloses compounds that are irreversible inhibitors of tyrosine kinases.

The generic Formula I presented in the PCT application encompasses the compound N-[4-(3-chloro-4-fluorophenylamino)-7-(3-morpholin-4-yl-propoxy)-quinazolin-6-yl]-acrylamide (herein "compound 1"), but compound 1 is not specifically named in the PCT application.

Compound 1 has the following chemical structure:

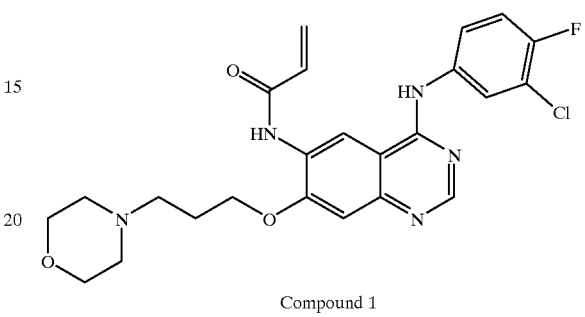

Compound 1

The PCT application discloses at Example 21 the compound N-[4-[(3-bromophenyl)amino]-7-[3-(4-morpholino)propoxy]quinazolin-6-yl]acrylamide, which has the following chemical structure:

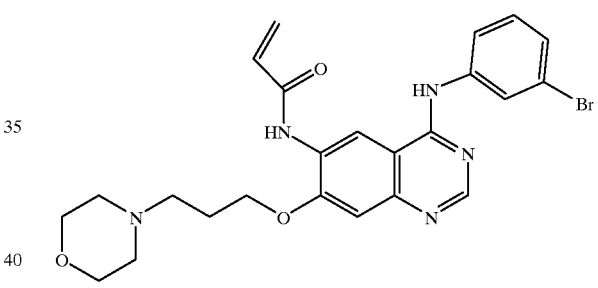

Example 21

Compound 1 differs from Example 21 in the substitution of the phenyl ring that is attached to the quinoline group via a nitrogen atom. The phenyl ring of compound 1 is substituted at the 3-position with chlorine and at the 4-position with fluorine. In contrast, the phenyl ring of Example 21 of the PCT application (herein "Example 21") is substituted only at the 3-position with bromine. While these two compounds are similar in structure, compound 1 shows surprising and unexpected properties in vivo when compared to Example 21 of the PCT application.

Even more surprising and unexpected is that compound 1 and Example 21 shown similar in vitro activity in certain assays, but exhibit significantly different in vivo activity.

SUMMARY OF THE INVENTION

The present invention provides the compound N-[4-(3-chloro-4-fluoro-phenylamino)-7-(3-morpholin-4-yl-propoxy)-quinazolin-6-yl]-acrylamide, or the pharmaceutically acceptable salts thereof.

Also provided is a pharmaceutically acceptable composition that comprises N-[4-(3-chloro-4-fluoro-phenylamino)-7-(3-morpholin-4-yl-propoxy)-quinazolin-6-yl]-acrylamide.

Also provided is a method of treating cancer, the method comprising administering to a patient having cancer a therapeutically effective amount of N-[4-(3-chloro-4-fluoro-phenylamino)-7-(3-morpholin-4-yl-propoxy)-quinazolin-6-yl]-acrylamide.

In a preferred embodiment of the method of treating cancer, the cancer is breast cancer.

In a preferred embodiment of the method of treating cancer, the cancer is colon cancer.

Also provided is a method of treating or preventing restenosis, the method comprising administering to a patient having restenosis or at risk of having restenosis a therapeutically affective amount of N-[4-(3-chloro-4-fluoro-phenylamino)-7-(3-morpholin-4-yl-propoxy)-quinazolin-6-yl]-acrylamide.

Also provided is a method of irreversibly inhibiting tyrosine kinases, the method comprising administering to a patient in need of tyrosine kinase inhibition a tyrosine kinase inhibiting amount of N-[4-(3-chloro-4-fluoro-phenylamino)-7-(3-morpholin-4-yl-propoxy)-quinazolin-6-yl]-acrylamide.

In a preferred embodiment of the method of irreversibly inhibiting tyrosine kinases, the tyrosine kinase is EGFR.

In a preferred embodiment of the method of irreversibly inhibiting tyrosine kinases, the tyrosine kinase is erbB2.

In a preferred embodiment of the method of irreversibly inhibiting tyrosine kinases, the tyrosine kinase is erbB4.

Also provided is a method of treating psoriasis, the method comprising administering to a patient having psoriasis a therapeutically effective amount of N-[4-(3-chloro-4-fluoro-phenylamino)-7-(3-morpholin-4-yl-propoxy)-quinazolin-6-yl]-acrylamide.

Also provided is a method of treating or preventing atherosclerosis, the method comprising administering to a patient having atherosclerosis or at risk of having atherosclerosis a therapeutically effective amount of N-[4-(3-chloro-4-fluoro-phenylamino)-7-(3-morpholin-4-yl-propoxy)-quinazolin-6-yl]-acrylamide.

Also provided is a method of treating endometriosis, the method comprising administering to a patient having endometriosis a therapeutically effective amount of N-[4-(3-chloro-4-fluoro-phenylamino)-7-(3-morpholin-4-yl-propoxy)-quinazolin-6-yl]-acrylamide.

Also provided is a method of inhibiting VEGF secretion, the method comprising administering to a patient in need of VEGF secretion inhibition a therapeutically effective amount of N-[4-(3-chloro-4-fluoro-phenylamino)-7-(3-morpholin-4-yl-propoxy)-quinazolin-6-yl]-acrylamide.

Also provided is a method of inhibiting the tyrosine phosphorylation of erbB3, the method comprising administering to a patient in need of the inhibition of tyrosine phosphorylation of erbB3 a therapeutically effective amount of N-[4-(3-chloro-4-fluoro-phenylamino)-7-(3-morpholin-4-yl-propoxy)-quinazolin-6-yl]-acrylamide.

DETAILED DESCRIPTION OF THE INVENTION

The present invention provides the compound N-[4-(3-chloro4-fluoro-phenylamino)-7-(3-morpholin-4-yl-propoxy)-quinazolin-6-yl]-acrylamide (Compound 1), or the pharmaceutically acceptable salts thereof.

Compound 1 is an irreversible inhibitor of tyrosine kinases, particularly EGFR tyrosine kinase. Other tyrosine kinases that can be inhibited by compound 1 include FGFR, PDGFR, c-src, erbB2, and erbB4. A therapeutically effective amount of compound 1 can be administered to a patient having cancer, or a patient having restenosis or at risk of having restenosis, or a patient having psoriasis, atherosclerosis or at risk of having atherosclerosis, or endometriosis. Those skilled in the art are readily able to identify patients having cancer, restenosis, psoriasis, atherosclerosis, or endometriosis, and patients who are at risk of having restenosis or atherosclerosis. For example, patients at risk of having restenosis are patients having undergone angioplasty, bypass, or graft procedures. Similarly, patients at risk of developing atherosclerosis include patients who are obese, eat high fat diets, have high cholesterol levels, or have hypertension. The term "patient" means animals such as dogs, cats, cows, sheep, and also includes humans.

The term "cancer" includes, but is not limited to, the following cancers:

breast;

ovary;

cervix;

prostate;

testis;

esophagus;

glioblastoma;

neuroblastoma;

stomach;

skin, keratoacanthoma;

lung, epidermoid carcinoma, large cell carcinoma, adenocarcinoma;

bone;

colon, adenocarcinoma, adenoma;

pancreas, adenocarcinoma;

thyroid, follicular carcinoma, undifferentiated carcinoma, papillary carcinoma;

seminoma;

melanoma;

sarcoma;

bladder carcinoma;

liver carcinoma and biliary passages;

kidney carcinoma;

myeloid disorders;

lymphoid disorders, Hodgkins, hairy cells;

buccal cavity and pharynx (oral), lip, tongue, mouth, pharynx;

small intestine;

colon-rectum, large intestine, rectum;

brain and central nervous system; and leukemia.

Preferred cancers that compound 1 can be used to treat include breast, colon, colon-rectum and ovarian cancers.

In addition, compound 1 can be used to treat patients in need of inhibition vascular endothelial growth factor (VEGF) secretion. Patients in need of inhibition of VEGF secretion include those having cancer, diabetic retinopathy, rheumatoid arthritis, psoriasis, restenosis, atherosclerosis, osteoporosis, endometriosis, persons undergoing embryo implantation, or persons having other diseases in which angiogenesis or neovascularization plays a role.

The compound of the present invention can be used to inhibit the tyrosine phosphorylation of erbB3. Patients in need of inhibition of tyrosine phosphorylation of erbB3 are patients having or at risk of having the diseases mentioned herein with regard to the inhibition of EGFR and the inhibition of VEGF secretion.

Compound 1 can be administered to humans and animals either orally, rectally, parenterally (intravenously, intramuscularly or subcutaneously), intracistemally, intravaginally, intraperitoneally, intravesically, locally (powders, ointments, or drops), or as a buccal or nasal spray. The compound can be administered alone or as part of a pharmaceutically acceptable composition that includes pharmaceutically acceptable excipients.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethylene-glycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound in a certain part of the intestinal tract in a delayed manner. Examples of embedding compositions which can be used are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compound, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compound of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compound or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine and the like (see, for example, S. M. Berge, et al., "Pharmaceutical Salts," *J. Pharm. Sci.*, 1977;66:1–19 which is incorporated herein by reference).

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compound of the present invention may be prepared according to conventional methods.

Examples of pharmaceutically acceptable, non-toxic amides of the compound of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compound of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A. C. S. Symposium Series, and in *Bioreversible Carriers in Drug Design*, ed. Edward B. Roche, American Pharmaceutical Association and Pergamon Press, 1987, both of which are incorporated herein by reference.

The compound of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

The compound of the present invention can exist in unsolvated as well as solvated forms with pharmaceutically acceptable solvents such as water, ethanol, and the like. In general, the solvated forms are considered equivalent to the unsolvated forms for the purposes of the present invention.

It is intended that the compound 1 be either synthetically produced or biologically produced, such as through metabolism.

The following examples illustrate particular embodiments of the invention and are not intended to limit the specification, including the claims, in any manner.

EXAMPLES

Compound 1 can be synthesized as follows:

N-[4-(3-Chloro-4-fluoro-phenylamino)-7-(3-morpholin-4yl-propoxy)-quinazolin-6-yl]-acrylamide Step A: 4-[(3-Chloro-4-fluorophenvl)aminol-7-fluoro-6-nitroguinazoline Powdered 4-chloro-7-fluoro-6-nitroquinazoline (*J. Med. Chem.*, 1996;39:918) (82.77 g, 363.7 mmol) was added in batches over 10 minutes to a mechanically stirred solution of 3-chloro-4-fluoroaniline (53.183 g, 365.3 mmol) and N,N-dimethylaniline (88.5 g, 730 mmol) in isopropanol (1.09 L) kept under nitrogen on an ice-bath. The ice-bath was removed at the end of the addition, and the mixture was stirred at 25° C. for 6 hours. The mixture was then cooled again on an ice-bath, and water (200 mL), followed by aqueous $Na_2CO_3$ solution (10% w/v, 200 mL) were added dropwise with stirring. After a further 10 minutes, the mixture was Buchner filtered, and the residual solid was rinsed with dilute $NaHCO_3$ solution (saturated/5, 2×100 mL), water (2×100 mL), and isopropanol (2×100 mL). The mixture was air dried, and then dried in a vacuum oven over $P_2O_5$ at 75° C. for 12 hours to give 4-[(3-chloro4-fluorophenyl)amino]-7-fluoro-6-nitroquinazoline (110.71 g, 90.4%) as a mustard yellow solid. $^1$H NMR (DMSO-$d_6$): δ 10.44 (s, 1H, NH), 9.51 (d, J=8.0 Hz, 1H, H-5), 8.67 (s, 1H, H-2), 8.07 (dd, J=2.7, 6.8 Hz, 1H, H-2'), 7.79 (d, J=12.4 Hz, 1H, H-8), 7.74 (ddd, J=2.7, 4.2, 9.0 Hz, 1H, H-6'), 7.43 (t, J=9.2 Hz, 1H, H-5').

Step B: 4-[(3-Chloro-4-fluorophenyl)amino]-7-[3-(4-morpholino)propoxy]-6-nitroguinazoline A solution of potassium trimethylsilanolate (57.73 g, 0.45 mol) in dimethyl sulfoxide (DMSO) (150 mL) was added dropwise over 50 minutes to a bright yellow slurry of 4-[(3-chloro4-fluorophenyl)amino]-7-fluoro-6-nitroquinazoline (50.503 g, 150 mmol) and 3-(4-morpholino)propan-l-ol (32.67 g, 225 mmol) in DMSO (250 mL), stirred vigorously under $N_2$ on a 25° C. water bath. Immediate deep red color, and by the end of the addition the reaction mixture was a deep red-black viscous mixture. After 6 hours the reaction mixture was poured slowly onto stirred ice-water (4 L) containing saturated $Na_2CO_3$ solution (150 mL). After standing for 13 hours the orange-red slurry was collected by Buchner filtration. The precipitate was rinsed with dilute NaOH solution (0.05 M, 500 mL; 0.02 M, 500 mL), dilute $NaHCO_3$ solution (saturated/5, 500 mL) and water (2×500 mL), and air dried for 4 hours, and then overnight at 50° C. in a vacuum oven over $P_2O_5$ to give 4-[(3-chloro-4-fluorophenyl)amino]-7-[3-(4-morpholino)propoxy]-6-nitroquinazoline (62.47 g, 89% corrected) as a bright orange-yellow solid. $^1$H NMR (DMSO-$d_6$): δ 10.11 (s, 1H, NH), 9.18 (s, 1H, H-5), 8.65 (s, 1H, H-2), 8.15 (dd, J=2.4, 6.8 Hz, 1H, H-2'), 7.79 (ddd, J=2.7, 4.3, 9.0 Hz, 1H, H-6'), 7.45 (t, J=9.0 Hz, 1 H, H-5'), 7.44 (s, 1H, H-8), 4.32 (t, J=6.1 Hz, ArOCH$_2$), 3.57 (t, J=4.5 Hz, 4 H, H-2 morpholino), 2.45 (t, J=6.5 Hz, 2 H, NCH$_2$), 2.34 (brs, 4 H, H-3 morpholino), 1.93 (pentet, J=6.5 Hz, 2 H, H-2 propoxy).

Step C: 6-Amino4-[(3-chloro-4-fluorolphenyl)aminol-7-[3-(4-morpholino)propoxylquinazoline A solution of 4-[(3-chloro-4-fluorophenyl)amino]-7-[3-(4-morpholino)propoxy]-6-nitroquinazoline (62.9 g, 136.2 mmol) in tetrahydrofuran (THF) (1200 mL) was hydrogenated over Raney Nickel (20 g) at 50 psi and 23° C. for 17.67 hours. Further Raney Nickel (20 g) was added, and the mixture was hydrogenated a further 4.33 hours under the same conditions. The reaction mixture was celite filtered, and the solvent was removed under reduced pressure to give 6-amino-4-[(3-chloro-4-fluorophenyl)amino]-7-[3-(4-morpholino)propoxy]quinazoline (57.81 g, 97.6% corrected) as a pale greenish solid. $^1$H NMR (DMSO-$d_6$): δ 9.40 (s, 1H, NH), 8.38 (s, 1H, H-2), 8.20 (dd, J=2.5, 7.0 Hz, 1H, H-2'), 7.79 (ddd, J=2.5, 4.5, 9.0 Hz, 1H, H-6'), 7.40 (s, 1H H-5), 7.40 (t, J=9.1 Hz, 1H, H-5'), 7.08 (s, 1 H, H-8), 5.38 (brs, NH$_2$), 4.19 (t, J=6.1 Hz, ArOCH$_2$), 3.58 (t, J=4.4 Hz, 4 H, H-2 morpholino), 2.49 (t, J=7.0 Hz, 2 H, NCH$_2$), 2.36 (brs, 4 H, H-3 morpholino), 1.97 (pentet, J=6.5 Hz, 2 H, H-2 propoxy).

Step D: N-[4-(3-Chloro-4-fluoro-phenylamino)-7-(3-morpholin-4-yl-propoxy)-quinazolin-6-yl]-acrylamide Isobutyl chloroformate (27.2 g, 0.20 mol) was added dropwise over 10 minutes to a solution of acrylic acid (14.40 g, 0.20 mol) and triethylamine (40.48 g, 0.40 mol) in THF (800 mL) stirred under nitrogen at 0° C. After a further 10 minutes, the white slurry was transferred to a–25° C. cooling bath and stirred under nitrogen for 20 minutes. 6-Amino-[(3-chloro4-fluorophenyl)amino]-7-[3-(4-morpholino) propoxy]quinazoline (43.19 g, 0.100 mol) in THF (500 mL) was added dropwise over 1.33 hours. The cooling bath was adjusted to–20° C., and after a further 2.33 hours, the reaction mixture was quenched by addition of water (100 mL) in one portion. After 20 minutes the reaction mixture was poured onto cracked ice (2 Kg), swirled, and gradually diluted with water (5 L). The mixture stood for 16 hours and was then Buchner filtered. The precipitate was rinsed with water (2×1 L), air dried for 18 hours, and then dried in a vacuum oven over $P_2O_5$ at 60° C. for 16 hours to give crude N-[4-[(3-chloro-4-fluorophenyl)amino]-7-[3-(4-morpholino)propoxy]quinazolin-6-yl]acrylamide (35.76 g, 73% uncorrected) as a greenish-yellow solid. The mother liquors precipitated further solid which was Buchner filtered, rinsed with water (1 L), and air dried for 14 hours to give further crude product (4.73 g, 10% uncorrected) as a greenish-yellow solid. Recrystallization of this material from DMSO recovered 55% of it as a pale yellow-khaki partial hydrate, mp 186.5–188.5° C. Calculated for $C_{24}H_{25}N_5O_3ClF.0.85H_2O$: C, 57.61; H, 5.37; N, 13.97%. Found: C, 57.51; H, 5.26; N, 13.88%. $^1$H NMR (DMSO-$d_6$): δ 9.81 (s, 1H, NH), 9.63 (s, 1H, NH), 8.87 (s, 1H, H-5), 8.54 (s, 1H, H-2), 8.15 (dd, J=2.5, 7.0 Hz, 1H, H-2'), 7.81 (ddd, J=2.7, 4.4, 9.0 Hz, 1H, H-6'), 7.43 (t, J=9.1 Hz, 1 H, H-5'), 7.30 (s, 1H, H-8), 6.72 (dd, J=10.1, 17.0 Hz, 1H, H-2 acryloyl), 6.32 (dd, J=9, 17.0 Hz, 1H, H-3 acryloyl), 5.83 (dd, J=1.9, 10.1, Hz, 1H, H-3 acryloyl), 4.27 (t, J=6.2 Hz, ArOCH$_2$), 3.58 (t, J=4.4 Hz, 4 H, H-2 morpholino), 2.48 (t, J=7.1 Hz, 2 H, NCH$_2$), 2.36 (brs, 4 H, H-3 morpholino), 2.00 (pentet, J=6.5 Hz, 2 H, H-2 propoxy). Mass spectrum APCI 489.2 (9), 488.2 (35), 487.2 (26), 486.2 (100).

The compound of Example 21 of PCT Application Number PCT/US97/05778 can be synthesized as follows:

EXAMPLE 21

N-[4-[(3-Bromophenyl)amino]-7-[3-(4-morpholino) propoxy]quinazolin-6-yl]acrylamide Sodium metal (27.6 mmol, 0.63 g) was added to a solution of 3-morpholinopropan-1-ol (22.0 mmol, 3.20 g) in THF (60 mL) under $N_2$. The resulting suspension was stirred at 20° C. for 2 hours and then cannulated into a solution of 4-[(3-bromophenyl)amino]-7-fluoro-6-nitro-quinazoline, *J. Med Chem.*, 1996(39):918) (2.0 g, 5.51 mmol) in THF (50 mL) under $N_2$. The solution was then heated at reflux for 24 hours before being diluted with water and extracted with EtOAc. The combined organic extracts were dried over anhydrous $Na_2SO_4$, concentrated under reduced pressure and chromatographed on alumina eluting with EtOAc/hexane (1:1) to MeOH/CH$_2$Cl$_2$/EtOAc (2:3:5) to give 4-[(3-bromophenyl)amino]-7-[(3-morpholino)propyloxy]-6-nitroquinazoline (1.75 g, 65%) as a yellow powder, mp (MeOH) 216–220° C.

$^1$H NMR [(CD$_3$)$_2$SO]: δ 10.12 (s, 1H, NH), 9.24 (s, 1H, aromatic), 8.69 (s, 1H, aromatic), 8.19 (t, J=1.8 Hz, 1H, H-2'), 7.88 (dt, $J_d$=7.8 Hz, $J_t$=1.4 Hz, 1H, H-6'), 7.49 (s, 1H, aromatic), 7.38 (t, J=8.0 Hz, 1 H, H-5'), 7.34 (dt, $J_d$=8.1 Hz, $J_t$=1.4 Hz, 1H, H-4'), 4.35 (t,J=6.2 Hz, 2H, CH$_2$CH$_2$CH$_2$O), 3.58 (t, J=4.6 Hz, 4H, morpholino methylene), 2.45 (t, J=7.0 Hz, 2H, NCH$_2$CH$_2$CH$_2$), 2.37 (br s, 4H, morpholino methylene), 1.94 (quintet, J=6.6 Hz, 2H, CH$_2$CH$_2$CH$_2$) $^{13}$CNMR: δ 157.76, 157.26, 153.76, 153.21, 140.32, 138.86, 130.37, 126.38, 124.26, 121.70, 121.13, 120.72, 110.11, 107.88, 67.87, 66.13 (×2), 54.42, 53.28 (×2), 25.30. Analysis calculated for $C_{21}H_{22}BrN_5O_4.0.75 H_2O$ requires: C, 50.3; H, 4.7; N, 14.0%. Found: C, 50.3; H, 4.4; N, 13.8%.

Freshly washed (1N HCl then distilled H$_2$O) iron powder (12 mmol, 0.686 g) was added in portions to a refluxing solution of the above nitroquinazoline (1.50 g, 3.07 mmol) in EtOF/H$_2$O (2:1, 80 mL) containing glacial acetic acid (2.0 mL). The resulting suspension was heated at reflux with vigorous stirring for 20 minutes then cooled, basified by the addition of concentrated NH$_3$ and filtered through a pad of celite. The celite pad was washed with EtOH before the filtrate was concentrated under reduced pressure, diluted with water, and extracted with EtOAc. The combined organic extracts were dried over anhydrous Na$_2$SO$_4$, concentrated under reduced pressure, and chromatographed on Grade III alumina eluting with CH$_2$Cl$_2$/EtOAc (1:1) to MeOH/EtOAc (2:98) to give 6-amino-4-[(3-bromophenyl)-amino]-7-[(3-morpholino)propyloxy]quinazoline (1.08 g, 77%) as a pale brown powder, mp (EtOAc/hexane) 158–160° C.

$^1$H NMR [(CD$_3$)$_2$SO], (400 MHz): δ 9.37 (s, 1H, NH), 8.40 (s, 1H, aromatic), 8.24 (t, J=1.9 Hz, 1H, H-2'), 7.86 (ddd, J=8.2, 0.8, 1.8 Hz, 1H, H-6'), 7.42 (s, 1H, aromatic), 7.30 (t, J=8.1 Hz, 1H, H-5'), 7.21 (ddd, J=8.2, 1.0, 1.9 Hz, 1H, H-4'), 7.09 (s, 1H, aromatic), 5.36 (s, 2H, NH$_2$), 4.20 (t, J=6.2 Hz, 2H, CH$_2$CH$_2$CH$_2$O), 3.59 (t, J=4.6 Hz, 4H, morpholino methylene), 2.50 (t, J=7.3 Hz, 2H, NCH$_2$CH$_2$CH$_2$), 2.39 (br s, 4H, morpholino methylene), 1.99 (quintet, J=6.7 Hz, 2H, CH$_2$CH$_2$CH$_2$). $^{13}$C NMR: 154.88, 151.94, 150.19, 144.84, 141.94, 138.50, 130.16, 124.66, 123.02, 121.09, 119.65, 110.42, 106.37, 100.81, 66.45, 66.14 (×2), 54.77, 53.29 (×2), 25.50. Analysis calculated for $C_{21}H_{24}BrN_5O_2.0.25 H_2O$ requires: C, 54.5; H, 5.3; N, 15.1%. Found: C, 54.6; H, 5.5; N, 15.0%.

To a stirred solution of the above 6-amino-quinazoline (0.50 g, 1.09 mmol), acrylic acid (6 mol, 6.54 mmol, 449 μL), and Et$_3$N (excess, 2.0 mL) in DMF (20 mL) under N$_2$ was added 1-(3-dimethyl-aminopropyl)-3-ethylcarbodiimide hydrochloride (EDCI.HCl) (3 mol, 3.27 mmol, 627 mg). The reaction was stirred at 0° C. for 15 minutes and then allowed to warm to room temperature and stirred for a further 2 hours. The solvent was removed under reduced pressure, and the resulting residue was diluted with saturated NaHCO$_3$ and repeatedly extracted with EtOAc. The combined organic extracts were washed with brine, dried over anhydrous Na$_2$SO4, and concentrated under reduced pressure. Chromatography on Grade III alumina eluting with EtOAc/hexane (9:1) to MeOH/EtOAc (2:98), N-[4-[( 3-bromophenyl)amino]-7-[(3-morpholino) propyloxy]-quinazolin-6-yl]acrylamide (329 mg, 59%) as a cream powder, mp (EtOAc/Et2O/hexane) 170-172° C.

$^1$H NMR [(CD$_3$)$_2$SO]: δ 9.78 (s, 1H, CONH), 9.62 (s, 1H, NH), 8.89 (s, 1H, aromatic), 8.56 (s, 1H, aromatic), 8.18 (t, J=1.9 Hz, 1H, H-2'), 7.88 (br d, J=8.2 Hz, 1H, H-6'), 7.34 (t,J=8.1 Hz, 1H, H-5'), 7.30 (s, 1H, aromatic), 7.27 (ddd, J=7.9, 1.4, 0.8 Hz, 1H, H-4'), 6.72 (dd, J=17.0, 10.2 Hz, 1H, CH$_2$CHCO), 6.33 (dd, J=17.0, 1.9 Hz, 1H, CH$_2$CHCO), 5.83 (dd, J=10.2, 1.9 Hz, 1H, CH$_2$CHCO), 4.27 (t, J=6.3 Hz, 2H, CH$_2$CH$_2$CH$_2$O), 3.58 (t, J=4.6 Hz, 4H, morpholino methylene), 2.48 (t, J=7.1 Hz, 2H, NCH$_2$CH$_2$CH$_2$), 2.38 (br s, 4H, morpholino methylene), 1.99 (quintet, J=6.7 Hz, 2H, CH$_2$CH$_2$CH$_2$) $^{13}$C NMR: δ163.49, 156.68, 154.96, 153.92, 149.19, 141.20, 131.58, 130.19, 127.16, 126.95, 125.52, 123.97, 121.03, 120.52, 116.78, 108.80, 107.28, 66.96, 66.14 (×2), 54.54, 53.28 (×2), 25.31. Analysis calculated for $C_{24}H_{26}BrN_5O_3 \cdot 0.5\ H_2O$ requires: C, 55.3; H, 5.2; N, 13.4%. Found: C, 55.3; H, 4.9; N, 13.3%.

COMPARATIVE STUDIES

Tissue Culture

A431 human epidermoid carcinoma cells and MDA-MB-453 cells were obtained from the American Type Culture Collection, Rockville, Md. and maintained as monolayers in dMEM (Dulbecco's modified eagle medium)/F12, 50:50 (Gibco/BRL, Bethesda, Md.) containing 10% fetal bovine serum. The cells were grown at 37° C. in a humidified atmosphere containing 5% $CO_2$ in air.

Purification of Epidermal Growth Factor Receptor Tyrosine Kinase

Human EGF receptor tyrosine kinase (EGFR) was isolated from A431 human epidermoid carcinoma cells by the following method. Cells were grown in roller bottles in dMEM/F12 media (Gibco/BRL, Bethesda, Md.) containing 10% fetal calf serum. Approximately $10^9$ cells were lysed in 2 volumes of buffer containing 20 mM Hepes, pH 7.4, 5 mM EGTA, 1% Triton X-100, 10% glycerol, 0.1 mM sodium orthovanadate, 5 mM sodium fluoride, 4 mM pyrophosphate, 4 mM benzamide, 1 mM DTT, 80 µg/mL aprotinin, 40 µg/mL leupeptin, and 1 mM phenylmethylsulfonyl fluoride (PMSF). After centrifugation at 25,000×g for 10 minutes, the supernatant was applied to a fast Q sepharose column (Pharmacia Biotech., Inc., Piscataway, N.J.) and eluted with a linear gradient from 0.1 M NaCl to 0.4 M NaCl in 50 mM Hepes, 10% glycerol, pH 7.4. Enzyme active fractions were pooled, divided into aliquots, and stored at −100° C. Fibroblast growth factor receptor (FGFR), platelet-derived growth factor (PDGF), insulin and c-src tyrosine kinases were obtained by methods well-known to those skilled in the art. For example, see Fry, et al., "Strategies For The Discovery Of Novel Tyrosine Kinase Inhibitors With Anticancer Activity, *Anticancer Drug Design*, 1994;9:331–351, which is hereby incorporated by reference.

Tyrosine Kinase Assays

Enzyme assays for $IC_{50}$ determinations were performed in 96-well filter plates (Millipore MADVN6550, Millipore, Bedford, Mass.). The total volume was 0.1 mL containing 20 mM Hepes, pH 7.4, 50 µM sodium vanadate, 40 mM magnesium chloride, 10 µM ATP containing 0.5 µCi of [$^{32}$P]ATP, 20 µg of poly Glutamic acid/tyrosine (Sigma Chemical Co., St. Louis, Mo.), 10 ng of EGF receptor tyrosine kinase, and appropriate dilutions of inhibitor. All components except the ATP are added to the well and the plate incubated with shaking for 10 minutes at 25° C. The reaction is started by adding [$^{32}$P]ATP, and the plate is incubated at 25° C. for 10 minutes. The reaction is terminated by addition of 0.1 mL of 20% trichloroacetic acid (TCA). The plate is kept at 4° C. for at least 15 minutes to allow the substrate to precipitate. The wells are then washed 5 times with 0.2 mL of 10% TCA and $^{32}$P incorporation determined with a Wallac beta plate counter. Assays using intracellular kinase domains of PDGF, FGF, and insulin receptors, as well as those for c-src were performed as described for the EGF receptor except that 10 mM Mangenese chloride was included in the reaction.

EGF—and Heregulin-dependent Tyrosine Phosphorvlation Assays

A431 human epidermoid carcinoma cells or MDA-MB-453 cells were grown in 6-well plates to about 80% confluency and then incubated in serum-free media for 18 hours. The cells were exposed to various concentrations of either compound 1 or Example 21 for 2 hours and then stimulated with either 100 ng/mL EGF (A431) or 10 ng/mL heregulin (MDA-MB453) for 5 minutes. Cell extracts were made, and the reduction in phosphotyrosine was determined by western blot.

Western Blotting Procedure

Extracts were made by lysing the monolayers in 0.2 mL of boiling Laemlli buffer (2% sodium dodecyl sulfate, 5% beta-mercaptoethanol, 10% glycerol and 50 mM Tris, pH 6.8), and the lysates were heated to 100° C. for 5 minutes. Proteins in the lysate were separated by polyacrylamide gel electrophoresis and electrophoretically transferred to nitrocellulose. The membrane was washed once in [10 mM Tris, pH 7.2, 150 mM NaCl, 0.01% sodium Azide] (TNA) and blocked overnight in TNA containing 5% bovine serum albumin and 1% ovalbumin. The membrane was blotted for 2 hours with antiphosphotyrosine antibody (UBI, Lake Placid, N.Y., 1 µg/mL in blocking buffer) and then washed twice in TNA, once in TNA containing 0.05% Tween-20 and 0.05% nonidet P-40 and twice in TNA. The membranes were then incubated for 2 hours in blocking buffer containing 0.1 µCi/mL of [$^{125}$I] protein A and then washed again as above. After the blots were dry, they were loaded into a film cassette and exposed to X-AR x-ray film for 1 to 7 days. Band intensities were determined with a laser densitometer.

The data in Table 1 show that Example 21 and compound 1 were about equally active against purified EGF receptor tyrosine kinase, EGF-mediated receptor autophosphorylation, and heregulin-mediated tyrosine phosphorylation in vitro.

TABLE 1

| Compound | EGF Receptor Tyrosine Kinase $IC_{50}$ (nM) | EGF-Mediated Receptor Autophosphorylation $IC_{50}$ (nM) | Heregulin-Medidated Tyrosine Phosphorylation $IC_{50}$ (nM) |
|---|---|---|---|
| Example 21 | 3.6 | 5.3 | 6.4 |
| compound 1 | 2.0 | 2.9 | 9.0 |

IN VIVO TUMOR INHIBITION ASSAY

The human epidermoid carcinoma, A431, was propagated in vivo by serial transplantation. This tumor model was selected for these studies because of its known dependence upon the EGF receptor for growth and its early stage responsiveness to monoclonal antibody therapy in vivo. In this experiment nude mice weighing 18–22 grams were implanted subcutaneously with 30 mg A431 tumor fragments in the region of the right axilla on Day 0. Tumors were allowed to grow to a mass of 100 to 150 mg, at which time the tumor bearing animals were randomized and distributed into treatment cages. Animals were treated perorally for 15 consecutive days with the isethionate salts of Example 21 and compound 1 in water. The isethionate salts can be prepared by titrating the compounds into solution with 2 equivalents of isethionic acid. Treatment was based on average group weight. The control animals received water. Evaluation of the experiment was based on tumor growth delay, T-C, defined as the difference, in days, for the treated and control tumors to reach an evaluation size of 750 mg. Data can also be represented as the percentage of tumor growth inhibition, defined as the tumor growth delay divided by the number of treatments times 100%. Larger tumor growth delays and tumor growth inhibition values are indicative of more active compounds. Statistical analysis was performed using JMP for Macintosh (SAS Institute, Inc., Cary, N.C.).

| Compound Tested | Dose (mg/kg) | Tumor Growth Delay (days) | Tumor Growth Inhibition (%) |
|---|---|---|---|
| Example 21 | 18 | 18.4 | 123 |
| Example 21 | 5 | 25.7 | 171 |
| Compound 1 | 18 | 41.3 | 275 |
| Compound 1 | 5 | 53.2 | 355 |

The values for compound 1 are significantly different from those for Example 21 based on the time required for individual tumors to reach 750 mg. p<0.05, student's t-test.

VEGF SECRETION ASSAY

Vascular endothelial growth factor (VEGF), which is also known as vascular permeability factor (VPF), is thought to be the major angiogenesis stimulator for most types of cancer. There are many inducers of tumor VEGF secretion, and two of the most potent are epidermal growth factor (EGF) and transforming growth factor alpha, both of which are ligands for EGF receptor (EGFR).

The inhibition of VEGF secretion results in an antiangiogenic effect and can lead to tumor regression, since even partial inhibition of VEGF secretion can lead to the destruction of newly formed immature blood vessels in tumors. (Benjamin L.E. and Keshel E., Conditional switching of VEGF expression in tumors: induction of endothelial cell shedding and regression of hemangioblastoma-like vessels by VEGF withdrawal. *Proc. Natl. Acad. Sci. USA*, 1997;94:8761–8766).

We have compared two EGFR tyrosine kinase inhibitors, compound 1 and Example 2 1, for their effect on A431 tumor cells. Against A431 tumors in vivo, compound 1 unexpectedly produced a greater antitumor response (T-C=53 days) than Example 21 (T-C=26 days). See the assay set forth above. Next, we examined the effect of both compounds on A431 secretion of VEGF. To our surprise, compound 1 was superior to Example 21 in inhibiting VEGF secretion from A431 cells in vitro. At 0.5 $\mu$M, compound 1 blocked EGF- or TGF-alpha stimulated VEGF secretion. In contrast, 0.5 $\mu$M Example 21 inhibited VEGF secretion to almost the same level as observed with 0.1 $\mu$M of compound 1. 0.1 $\mu$M of the compound 1 inhibited EGF-stimulated VEGF secretion by 63% and 5 0.5 $\mu$M inhibited by 86%. In contrast, 0.1 $\mu$M of Example 21 inhibited EGF-stimulated VEGF secretion by 48% and 0.5 $\mu$M of Example 21 inhibited EGF-stimulated VEGF secretion by 57%. Similar results were obtained using TGF-alpha to stimulate VEGF secretion in place of EGF. 0.5 $\mu$M of compound 1 inhibited TGF-alpha stimulated VEGF secretion by greater than 80% whereas the same concentration of Example 21 inhibited VEGF secretion by 57%. Compound 1 also appeared to inhibit the basal level of VEGF secretion from A431 cells whereas Example 21 had no effect.

Methods

A431 human epidermoid carcinoma cells, obtained from the American Type Culture Collection (Rockville, Md.) were cultured in Dulbecco's MEM/F12 media (DMEM/F12) supplemented with 10% fetal bovine serum. Prior to drug and growth factor treatment, cells were washed three times in serum free DMEM/F12. Cells were treated for 2 hours with the indicated concentration of compound 1 or Example 21 prior to the addition of either 10 ng/mL EGF or TGF-alpha. After 48 hours of incubation at 37° C., media was removed and stored frozen at–70° C. VEGF ELISA assays (Intergen, Co., Purchase, N.Y.) are performed on media samples following the manufacturer's instructions.

The results of this assay are shown below in tabular form.

| Treatment | VEGF secretion (pg/$10^5$ cells ± SE) | Percent Inhibition |
|---|---|---|
| Serum Free Media (SF) | 490 ± 32 | |
| SF + 0.1 $\mu$M compound 1 | 280 ± 41 | 43 |
| SF + 0.5 $\mu$M compound 1 | 250 ± 46 | 49 |
| SF + 0.1 $\mu$M Example 21 | 600 ± 37 | 0 |
| SF + 0.5 $\mu$M Example 21 | 440 ± 110 | 10 |
| SF + 10 ng/mL EGF | 3980 ± 85 | |
| SF + EGF + 0.1 $\mu$M compound 1 | 1490 ± 170 | 63 |
| SF + EGF + 0.5 $\mu$M compound 1 | 560 ± 29 | 86 |
| SF + EGF + 0.1 $\mu$M Example 21 | 2070 ± 160 | 48 |
| SF + EGF + 0.5 $\mu$M Example 21 | 1710 ± 65 | 57 |
| SF + TGF-alpha | 4034 ± 190 | |
| SF + TGF + 0.1 $\mu$M compound 1 | 1976 ± 37 | 51 |
| SF + TGF + 0.5 $\mu$M compound 1 | 766 ± 75 | 81 |
| SF + TGF + 0.1 $\mu$M Example 21 | 3065 ± 161 | 24 |
| SF + TGF + 0.5 $\mu$M Example 21 | 1734 ± 21 | 57 |

What is claimed is:

1. The compound: N-[4-(3-chloro-4-fluoro-phenylamino)-7-(3-morpholin-4-yl-propoxy)-quinazolin-6-yl]-acrylamide, or the pharmaceutically acceptable salts thereof.

2. A pharmaceutically acceptable composition that comprises a compound of claim 1.

3. A method of treating cancer, the method comprising administering to a patient having cancer a therapeutically effective amount of a compound of claim 1.

4. The method of claim 3 wherein the cancer is breast cancer.

5. The method of claim 3 wherein the cancer is colon cancer.

6. A method of treating or preventing restenosis, the method comprising administering to a patient having restenosis or at risk of having restenosis a therapeutically affective amount of a compound of claim 1.

7. A method of irreversibly inhibiting tyrosine kinases, the method comprising administering to a patient in need of tyrosine kinase inhibition a tyrosine kinase inhibiting amount of a compound of claim 1.

8. The method of claim 7 wherein the tyrosine kinase is EGFR.

9. The method of claim 7 wherein the tyrosine kinase is erbB2.

10. The method of claim 7 wherein the tyrosine kinase is erbB4.

11. A method of inhibiting the tyrosine phosphorylation of erbB3, the method comprising administering to a patient in need of the inhibition of tyrosine phosphorylation of erbB3 a therapeutically effective amount of N-[4-(3-chloro-4-fluoro-phenylamino)-7-(3-morpholin-4-yl-propoxy)-quinazolin-6-yl]-acrylamide.

12. A method of treating psoriasis, the method comprising administering to a patient having psoriasis a therapeutically effective amount of a compound of claim 1.

13. A method of treating or preventing atherosclerosis, the method comprising administering to a patient having atherosclerosis or at risk of having atherosclerosis a therapeutically effective amount of a compound of claim 1.

14. A method of treating endometriosis, the method comprising administering to a patient having endometriosis a therapeutically effective amount of a compound of claim 1.

15. A method of inhibiting VEGF secretion, the method comprising administering to a patient in need of VEGF secretion inhibition a therapeutically effective amount of a compound of claim 1.

* * * * *